(12) United States Patent
Horigome et al.

(10) Patent No.: US 8,420,128 B2
(45) Date of Patent: Apr. 16, 2013

(54) METHOD OF IMPARTING HEAT RESISTANCE TO LACTOFERRIN

(75) Inventors: Ayako Horigome, Zama (JP); Mai Murata, Zama (JP); Koji Yamauchi, Zama (JP); Mitsunori Takase, Zama (JP); Yasuhiro Takeda, Zama (JP); Junichi Hashimoto, Zama (JP); Ikumi Kojima, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 303 days.

(21) Appl. No.: 12/867,979

(22) PCT Filed: Mar. 31, 2009

(86) PCT No.: PCT/JP2009/001486
§ 371 (c)(1),
(2), (4) Date: Aug. 17, 2010

(87) PCT Pub. No.: WO2009/122719
PCT Pub. Date: Oct. 8, 2009

(65) Prior Publication Data
US 2010/0310673 A1    Dec. 9, 2010

(30) Foreign Application Priority Data

Mar. 31, 2008 (JP) ................... 2008-093971
Dec. 26, 2008 (JP) ................... 2008-335119

(51) Int. Cl.
 *A01N 59/20* (2006.01)
 *A61K 33/34* (2006.01)

(52) U.S. Cl.
 USPC ........................................................ 424/638

(58) Field of Classification Search .................. None
See application file for complete search history.

(56) References Cited

U.S. PATENT DOCUMENTS

| 5,376,379 A | 12/1994 | Fabre et al. |
| 6,245,568 B1 | 6/2001 | Volkin et al. |
| 6,251,678 B1 | 6/2001 | Volkin et al. |
| 2001/0021385 A1 | 9/2001 | Volkin et al. |
| 2008/0153741 A1* | 6/2008 | Matsunaga et al. ............... 514/8 |
| 2008/0255340 A1* | 10/2008 | Naidu ........................... 530/350 |

FOREIGN PATENT DOCUMENTS

| EP | 0437958 A1 | 7/1991 |
| JP | 60-19742 B2 | 5/1985 |
| JP | 2688098 B2 | 12/1997 |
| JP | 10-176000 A | 6/1998 |
| JP | 3223958 B2 | 10/2001 |
| JP | 3230239 B2 | 11/2001 |
| JP | 2002-536340 A | 10/2002 |
| JP | 2002-540167 A | 11/2002 |
| JP | 2003-137808 A | 5/2003 |
| JP | 2003137808 A * | 5/2003 |
| JP | 2004-352669 A | 12/2004 |
| JP | 2009-519284 A | 5/2009 |
| WO | 2006/016595 A1 | 2/2006 |
| WO | 20071068495 A1 | 6/2007 |

OTHER PUBLICATIONS

Gelbwasser, WPI Journal, vol. C1: 1 (1999).*
European Search Report dated Apr. 4, 2012, issued in corresponding European Patent Application No. 09727101.9.
Journal of Pediatrics, vol. 90, p. 29, 1977.
Advances in Experimental Medicine and Biology, vol. 357, p. 219, 1994.
International Search Report of PCT/JP2009/001486, Mailing Date of Jun. 16, 2009.
Notification of Transmittal of Translation of the International Preliminary Report on Patentability (Form PCT/IB/338) of International Application No. PCT/JP2009/001486 mailed Dec. 23, 2010 with Forms PCT/IB/373 and PCT/ISA/237.

* cited by examiner

*Primary Examiner* — James H Alstrum Acevedo
*Assistant Examiner* — Thor Nielsen
(74) *Attorney, Agent, or Firm* — Westerman, Hattori, Daniels & Adrian, LLP

(57) ABSTRACT

An agent for thermally stabilizing lactoferrin, which comprises a nucleic acid as an active ingredient, can be added to lactoferrin to impart thermal stability to lactoferrin. Thermally stabilized lactoferrin can be heat-sterilized at a pH value around a neutral pH value while keeping its activity.

11 Claims, No Drawings

METHOD OF IMPARTING HEAT RESISTANCE TO LACTOFERRIN

TECHNICAL FIELD

The present invention relates to an agent for stabilizing lactoferrin against heat treatment including a nucleic acid as an active ingredient and a composition including a nucleic acid and lactoferrin in a mass ratio of nucleic acid to lactoferrin of 0.09 to 6.3.

The present invention also relates to an agent for contributing the heat-stability of lactoferrin including a nucleic acid and a metal as active ingredients and a composition including a nucleic acid, a metal, and lactoferrin, wherein a molar ratio of the metal to the lactoferrin is 0.04 to 3.0 and a mass ratio of the nucleic acid to the lactoferrin is 0.09 to 6.3. Further, the present invention also relates to a method for heat-sterilizing lactoferrin including the step of adding an agent for contributing the heat-stability of lactoferrin including a nucleic acid and a metal as active ingredients.

BACKGROUND ART

A nucleic acid is a biopolymer present in the nucleus of cells of living organisms, and is made of nucleotides linked together by phosphoester bonds. Each nucleotide is made of a sugar, a base, and phosphoric acid. Nucleic acids are broadly divided, depending on the kind of sugar used, into deoxyribonucleic acid (DNA) having 2-deoxyribose and ribonucleic acid (RNA) having ribose. These nucleic acids are deeply involved in storage of genetic information and transmission of information in the cells of a living body.

Further, it is known that both DNA and RNA contain four kinds of bases and are composed of two nucleotide chains forming a double helix.

In recent years, it has become known that intake of nucleic acids has an effect on, for example, cell metabolism, immune function, brain function, and lipid metabolism and provides a skin-lightening effect. In order to utilize such effects of nucleic acids, nucleic acid-containing foods, beverages, health foods, and raw materials for pharmaceutical products are produced and sold.

For example, a thermally-stabilized prostaglandin composition including bioactive prostaglandin and RNA or DNA is known (see, for example, Patent Document 1). The composition is produced by adding prostaglandin in the form of crystal, powder, or solution to an aqueous solution with a pH of 7 to 8 containing DNA or RNA in such an amount that the weight ratio of DNA or RNA to prostaglandin to be added is usually 10:1 to 1000:1, preferably 50:1 to 400:1.

Further, a hot spring water-based composition including liposomes of hot spring water stabilized in a DNA gel is known (see, for example, Patent Document 2).

However, it has not been known that nucleic acids contribute heat-stability to protein.

Lactoferrin (LF) is an iron-binding protein contained in tears, saliva, peripheral blood, milk, etc of a living body. It has been reported that lactoferrin has various physiological activities such as antibacterial effect against harmful bacteria, enteral iron absorption-promoting effect, immunostimulating effect, cell growth effect, anti-inflammatory effect, and bifidobacteria growth effect.

As described above, lactoferrin having such excellent physiological activities is a protein contained in, for example, mammalian milk, and is therefore very safe for ingestion. For this reason, lactoferrin is used in various products, and various lactoferrin-containing products such as foods, beverages, processed foods, pharmaceutical products, and modified powdered milk for infants are commercially available.

However, it is known that lactoferrin is unstable to heat, and particularly when the pH of lactoferrin is in the neutral region, its physiological activities are almost lost by heating at 62.5° C. for 30 minutes and are completely lost by heating at 70° C. for 15 minutes (see, for example, Non-Patent Document 1). Further, it has been reported that the iron-binding ability of lactoferrin is adversely affected by denaturation caused by heating (see, for example, Non-Patent Document 2).

On the other hand, it has been disclosed that when the pH of a lactoferrin solution is in the range of 1.0 to 6.5, particularly in the range of 2.0 to 6.0, lactoferrin is stable to heat (see, for example, Patent Document 3).

As lactoferrin having improved thermal stability, a lactoferrin composition containing soybean polysaccharide, xanthan gum, or the like as a stabilizer has been reported (see, for example, Patent Document 4).

Patent Document 1: JP-B No. S60-19742
Patent Document 2: Japanese Patent No. 3230239
Patent Document 3: Japanese Patent No. 2688098
Patent Document 4: JP-A No. 2004-352669
Patent Document 5: Japanese Patent No. 3223958
Non-Patent Document 1: Journal of Pediatrics, vol. 90, p. 29, 1977
Non-Patent Document 2: Advances in Experimental Medicine and Biology, vol. 357, p. 219, 1994

DISCLOSURE OF THE INVENTION

Problems to be Solved by the Invention

As described above, lactoferrin has come to be added to various foods, beverages, processed foods, and pharmaceutical products because of its excellent physiological activities and safety. However, production processes of such products generally involve heat sterilization used as a simple and reliable sterilization method, in spite of the fact that, as described above, lactoferrin is unstable to heat and it cannot be expected that thermally-denatured lactoferrin will exhibit effective physiological activities. This imposes a significant constraint on the production of lactoferrin-containing products. Under the circumstances, various methods for improving thermal stability of lactoferrin have been heretofore developed.

According to findings described in the above-mentioned Patent Document 3, the loss of activities of lactoferrin due to thermal denaturation can be reduced by adjusting the pH of lactoferrin to a value in the range of 1.0 to 6.5 before heat sterilization. However, this method is disadvantageous in that the production process of a product becomes complicated because it is necessary to once change the pH of the product from the neutral to acidic region. Further, there is also a fear that one or more other active ingredients contained in the product are adversely affected by heating under acidic conditions.

The above-mentioned Patent Document 4 discloses, as its preferred embodiment, the use of soybean polysaccharide, xanthan gum, or the like as a stabilizer in an amount of 0.5 to 100 times by weight the amount of lactoferrin used. However, addition of a large amount of the stabilizer imposes a significant constraint on the production of foods containing lactoferrin. More specifically, addition of soybean polysaccharide or a gum such as xanthan gum to a product increases the viscosity of the product, which affects the physical properties of the product. Therefore, it is difficult to add the stabilizer in such a large amount. Further, in the test example of the Patent Document 4, the concentration of lactoferrin is limited to a relatively low level of 8 mg % to 20 mg %, and there is no description about the effect of the stabilizer at the time when the concentration of lactoferrin is high.

The above-mentioned Patent Document 5 discloses that two or more kinds of metal ions are added to stabilize lactoferrin in such an amount that the molar ratio of metal ions to lactoferrin is 3:1 to 500:1. However, the metal ions have the effect of promoting oxidation of fats and oils, and therefore the amount of metal ions to be added is preferably small from the viewpoint of inhibiting oxidation of foods, beverages, etc. containing fats and oils. Further, also from the viewpoint of reducing a metallic smell, the amount of metal ions to be added is preferably small.

As described above, various methods for preventing thermal denaturation of lactoferrin caused by heating, that is, for improving thermal stability of lactoferrin have been developed, but these conventional methods have a problem that the amount of a protein to be added is limited because the blending ratio among raw materials is limited by the amount used, appearance, taste, viscosity, pH, and color of the raw materials. Particularly, since lactoferrin has low thermal stability in the neutral pH region, keeping thermal stability of lactoferrin in the neutral pH region is an issue that needs to be addressed. Further, there has been a demand for development of a method for easily improving thermal stability of lactoferrin, which can exhibit the effect of improving thermal stability of lactoferrin without restricting product design etc. even when the amounts of raw materials other than lactoferrin are small.

It is therefore an object of the present invention to provide a method for improving thermal stability of lactoferrin, that is, a method for stabilizing lactoferrin against heat treatment. More particularly, it is an object of the present invention to provide a method for stabilizing lactoferrin against heat treatment at a pH in the neutral region.

Means for Solving the Problems

The present inventors have extensively studied, and as a result have found that addition of a nucleic acid to lactoferrin significantly improves the heat-stability of the lactoferrin and that such a heat stability-improving (i.e., thermally-stabilizing) effect is effectively exhibited even when the pH of lactoferrin is in a pH range around neutral. Namely, the present inventors have found that the above object can be achieved by adding a nucleic acid to lactoferrin as an agent for stabilizing lactoferrin against heat treatment, and this finding has led to the completion of the present invention.

Further, the present inventors have also found that addition of a nucleic acid and a small amount of metal to lactoferrin makes it possible to further improve the heat-stability of the lactoferrin as compared to a case where only a nucleic acid is added to lactoferrin.

In order to achieve the above object, a first aspect of the present invention is directed to an agent for contributing the heat-stability of lactoferrin including a nucleic acid as an active ingredient.

According to a preferred embodiment of the first aspect of the present invention, the nucleic acid has a molecular weight of 60 to 1200 kDa, the nucleic acid is derived from soft roe, and the agent contributes heat-stability to lactoferrin at a pH in the range of 6 to 9.

A second aspect of the present invention is directed to an agent for contributing the heat-stability of lactoferrin including a nucleic acid and a metal as active ingredients.

According to a preferred embodiment of the second aspect of the present invention, the agent is used so that the mass ratio of the nucleic acid to lactoferrin is 0.09 to 6.3 and the molar ratio of the metal to lactoferrin is 0.04 to 3.0, the nucleic acid has a molecular weight of 60 to 1200 kDa, the nucleic acid is derived from soft roe, and the metal is at least one selected from iron, zinc, and copper. According to a further preferred embodiment of the second aspect of the present invention, the metal is copper.

A third aspect of the present invention is directed to a composition including a nucleic acid and lactoferrin in a mass ratio of nucleic acid to lactoferrin of 0.09 to 6.3. According to a preferred embodiment of the third aspect of the present invention, the lactoferrin has improved heat-stability and the nucleic acid has a molecular weight of 60 to 1200 kDa.

A fourth aspect of the present invention is directed to a composition including a nucleic acid, a metal, and lactoferrin, wherein a weight ratio of the nucleic acid to the lactoferrin is 0.09 to 6.3 and a molar ratio of the metal to the lactoferrin is 0.04 to 3.0.

According to a preferred embodiment of the fourth aspect of the present invention, the lactoferrin has improved heat-stability, the nucleic acid has a molecular weight of 60 to 1200 kDa, and the metal is at least one selected from iron, zinc, and copper. According to a further preferred embodiment of the fourth aspect of the present invention, the metal is copper.

A fifth aspect of the present invention is directed to a pharmaceutical product including the composition according to the third or fourth aspect of the present invention.

A sixth aspect of the present invention is directed to a food or beverage including the composition according to the third or fourth aspect of the present invention.

A seventh aspect of the present invention is directed to a feed including the composition according to the third or fourth aspect of the present invention.

An eighth aspect of the present invention is directed to a method for heat-sterilizing lactoferrin, including the step of adding an agent for contributing the heat-stability of lactoferrin including a nucleic acid as an active ingredient.

According to a preferred embodiment of the eighth aspect of the present invention, the agent is used so that the mass ratio of the nucleic acid to lactoferrin is 0.09 to 6.3, the nucleic acid has a molecular weight of 60 to 1200 kDa, and the nucleic acid is derived from soft roe.

A ninth aspect of the present invention is directed to a method for heat-sterilizing lactoferrin, including the step of adding an agent for contributing the heat-stability of lactoferrin including a nucleic acid and a metal as active ingredients.

According to a preferred embodiment of the ninth aspect of the present invention, the agent is used so that the mass ratio of the nucleic acid to lactoferrin is 0.09 to 6.3 and the molar ratio of the metal to lactoferrin is 0.04 to 3.0, the nucleic acid has a molecular weight of 60 to 1200 kDa, the nucleic acid is derived from soft roe, and the metal is at least one selected from iron, zinc, and copper. According to a further preferred embodiment of the ninth aspect of the present invention, the metal is copper.

Namely, it is an object of the present invention to provide an agent for improving thermal stability of lactoferrin.

Further, it is also an object of the present invention to provide a lactoferrin composition having improved thermal stability.

Further, it is also an object of the present invention to provide a pharmaceutical product, food, beverage, or feed including the lactoferrin composition having improved thermal stability.

Further, it is also an object of the present invention to provide a method for heat-sterilizing lactoferrin including using the agent for improving thermal stability of lactoferrin.

According to the present invention, it is possible to sterilize lactoferrin at high temperature without causing denaturation, aggregation, or precipitation of the lactoferrin. Further, it is also possible to sterilize lactoferrin at high temperature without impairing its functions even in the neutral pH region in which lactoferrin has low thermal stability.

Therefore, the present invention provides the following (1) to (9).

(1) An agent for contributing the heat-stability to lactoferrin including a nucleic acid as an active ingredient.

(2) The agent according to the above (1), wherein the nucleic acid has a molecular weight of 60 to 1200 kDa.

(3) The agent according to the above (1) or (2), wherein the nucleic acid is derived from soft roe.

(4) The agent according to any one of the above (1) to (3), which contributes heat-stability to lactoferrin at a pH in a range of 6 to 9.

(5) A composition including a nucleic acid and lactoferrin in a mass ratio of nucleic acid to lactoferrin of 0.09 to 6.3.

(6) The composition according to the above (5), wherein the lactoferrin has improved heat-stability.

(7) A pharmaceutical product including the composition according to the above (5) or (6).

(8) A food or beverage including the composition according to the above (5) or (6).

(9) A feed including the composition according to the above (5) or (6).

The present invention also provides the following (11) to (28).

(11) An agent for contributing the heat-stability to lactoferrin including a nucleic acid and a metal as active ingredients.

(12) The agent according to the above (11), which is used so that a mass ratio of the nucleic acid to lactoferrin is 0.09 to 6.3 and a molar ratio of the metal to lactoferrin is 0.04 to 3.0.

(13) The agent according to the above (11) or (12), wherein the nucleic acid has a molecular weight of 60 to 1200 kDa.

(14) The agent according to any one of the above (11) to (13), wherein the nucleic acid is derived from soft roe.

(15) The agent according to any one of the above (11) to (14), wherein the metal is copper.

(16) A composition including a nucleic acid, a metal, and lactoferrin, wherein a mass ratio of the nucleic acid to the lactoferrin is 0.09 to 6.3 and a molar ratio of the metal to the lactoferrin is 0.04 to 3.0.

(17) The composition according to the above (16), wherein the lactoferrin has improved heat-stability.

(18) The composition according to the above (16) or (17), wherein the nucleic acid has a molecular weight of 60 to 1200 kDa.

(19) The composition according to any one of the above (16) to (18), wherein the nucleic acid is derived from soft roe.

(20) The composition according to any one of the above (16) to (19), wherein the metal is copper.

(21) A pharmaceutical product including the composition according to any one of the above (6) to (20).

(22) A food or beverage including the composition according to any one of the above (6) to (20).

(23) A feed including the composition according to any one of the above (6) to (20).

(24) A method for heat-sterilizing lactoferrin, including the step of adding an agent for contributing the heat-stability to lactoferrin including a nucleic acid and a metal as active ingredients.

(25) The method according to the above (24), wherein the agent is used so that a mass ratio of the nucleic acid to lactoferrin is 0.09 to 6.3 and a molar ratio of the metal to lactoferrin is 0.04 to 3.0.

(26) The method according to the above (24) or (25), wherein the nucleic acid has a molecular weight of 60 to 1200 kDa.

(27) The method according to any one of the above (24) to (26), wherein the nucleic acid is derived from soft roe.

(28) The method according to any one of the above (24) to (27), wherein the metal is copper.

Further, the present invention also provides the following (31) and (32).

(31) An agent for stabilizing lactoferrin against heat treatment including a nucleic acid as an active ingredient.

(32) An agent for stabilizing lactoferrin against heat treatment including a nucleic acid.

According to the present invention, it is possible to contribute thermal stability (heat-stability) to lactoferrin. Therefore, the present invention also provides an agent for stabilizing against heat treatment for lactoferrin, an agent for stabilizing lactoferrin against heat treatment, an agent for improving heat-stability of lactoferrin, an improving agent for lactoferrin in heat-stability, a heat-stabilizer of lactoferrin, a lactoferrin additive for heat-stabilizing in sterilization, an agent for sterilization of lactoferrin, and a heat-stabilizing agent for pasteurization of lactoferrin.

Further, the present invention also provides the following (33) to (36).

(33) The agent for stabilizing lactoferrin against heat treatment according to the above (31) or (32), which is used in a pH range of 6 to 9.

(34) The agent for stabilizing lactoferrin against heat treatment according to the above (31) or (32), which is intended to stabilize lactoferrin against heat treatment in a pH range of 6 to 9.

(35) The agent for stabilizing lactoferrin against heat treatment according to anyone of the above (31) to (34), wherein the nucleic acid has a molecular weight of 60 to 1200 kDa.

(36) The agent for stabilizing lactoferrin against heat treatment according to any one of the above (31) to (35), wherein the nucleic acid is derived from soft roe.

According to the present invention, lactoferrin is effectively stabilized against heat treatment over the entire pH range including a pH range around neutral in which it has been heretofore difficult to stabilize lactoferrin against heat treatment. The stabilization of lactoferrin against heat treatment is preferably performed in a pH range around neutral, for example, in a pH range of 6 to 9, 6 to 8, 6.5 to 9, 6.5 to 8, 6.5 to 7.5, 7 to 9, or 7 to 8. Therefore, the present invention also provides an agent for stabilizing lactoferrin against heat treatment intended for use in the pH range of 6 to 9, 6 to 8, 6.5 to 9, 6.5 to 8, 6.5 to 7.5, 7 to 9, or 7 to 8. In order to ensure such a preferred pH range, the agent for stabilizing lactoferrin against heat treatment according to the present invention may contain a pH adjusting component in addition to a nucleic acid. That is, the present invention also provides an agent for stabilizing lactoferrin against heat treatment including, as active ingredients, a nucleic acid and a pH adjusting component for adjusting the pH of lactoferrin to a value within the above preferred range.

In the present invention, a crude nucleic acid extract or a nucleic acid partial purificant can be used as a nucleic acid. The nucleic acid used in the present invention does not need to have a specific base sequence and can have a molecular weight within a wide range. As the nucleic acid, a nucleic acid and/or a salt thereof can be used. Examples of the salt include sodium salts and potassium salts.

Further, the present invention also provides the following (37) to (40).

(37) The agent for stabilizing lactoferrin against heat treatment according to anyone of the above (31) to (36), further including a metal.

(38) The agent for stabilizing lactoferrin against heat treatment according to the above (37), wherein the metal is at least one selected from the group consisting of iron, zinc, and copper.

(39) The agent for stabilizing lactoferrin against heat treatment according to the above (37), wherein the metal is copper.

(40) The agent for stabilizing lactoferrin against heat treatment according to any one of the above (31) to (39), which is an agent for sterilization of lactoferrin.

The agent for stabilizing lactoferrin against heat treatment according to the present invention may further include a metal in addition to a nucleic acid. This makes it possible to further improve the thermal stability of lactoferrin. In this case, since the amount of the metal to be added is very small, there is no fear that the flavor of products will be adversely affected by a metallic smell. As the metal, a metal and/or a salt thereof can be used. Examples of the salt include chlorides, sulfates, phosphates, and gluconates. According to a preferred embodiment of the present invention, the metal is copper. In this case, the agent is used so that the mass ratio of elemental copper (mass) to the nucleic acid (mass) is in the range of, for example, 0 to $1 \times 10^{-2}$, 0 to $1 \times 10^{-3}$, or 0 to $1 \times 10^{-4}$ or in the range of, for example, $1 \times 10^{-6}$ to $1 \times 10^{-2}$, $1 \times 10^{-6}$ to $1 \times 10^{-3}$, or $1 \times 10^{-6}$ to $1 \times 10^{-4}$.

Further, the present invention also provides the following (41) to (45).

(41) A lactoferrin composition including a nucleic acid and lactoferrin.

(42) A lactoferrin composition including a nucleic acid and lactoferrin, wherein the lactoferrin is thermally stabilized.

(43) The lactoferrin composition according to the above (41) to (42), further including a metal.

(44) A thermally-stabilized lactoferrin composition including the agent for stabilizing lactoferrin against heat treatment according to any one of the above (31) to (40) and lactoferrin.

(45) The lactoferrin composition according to any one of the above (41) to (44), wherein a mass ratio of the nucleic acid (mass) to the lactoferrin (mass) is in a range of 0.09 to 6.3.

The lactoferrin contained in the lactoferrin composition according to the present invention is thermally stabilized and is therefore prevented from being deactivated by thermal denaturation, which makes it possible to appropriately subject the lactoferrin composition according to the present invention to heat treatment for the purpose of heat sterilization etc. Therefore, the lactoferrin composition according to the present invention is suitable for use as a raw material of pharmaceutical products, foods, and beverages usually requiring heat sterilization or the like.

Further, the present invention also provides the following (46) to (54).

(46) Use of a nucleic acid to stabilize lactoferrin against heat treatment.

(47) Use of a nucleic acid to heat-sterilize lactoferrin.

(48) A method for stabilizing lactoferrin against heat treatment including adding a nucleic acid to lactoferrin.

(49) A method for stabilizing lactoferrin against heat treatment including the step of adding a nucleic acid to lactoferrin.

(50) Use of a nucleic acid and a metal to stabilize lactoferrin against heat treatment.

(51) The method according to the above (48), wherein a metal is further added in addition to the nucleic acid.

(52) The method according to the above (49), wherein in the step of adding a nucleic acid to lactoferrin, a metal is further added to lactoferrin, or further including the step of adding a metal to lactoferrin before or after the step of adding a nucleic acid to lactoferrin.

(53) A method for stabilizing lactoferrin against heat treatment including adding the agent for stabilizing lactoferrin against heat treatment according to any one of the above (31) to (40) to lactoferrin.

(54) A method for stabilizing lactoferrin against heat treatment including the step of adding the agent for stabilizing lactoferrin against heat treatment according to any one of the above (31) to (40) to lactoferrin.

The method for stabilizing lactoferrin against heat treatment according to a preferred embodiment of the present invention is suitable for pretreating lactoferrin or a composition including lactoferrin before heat treatment performed for the purpose of heat sterilization etc.

Therefore, the present invention also provides the following (55).

(55) A method for heat-sterilizing lactoferrin including the steps of: stabilizing lactoferrin against heat treatment by adding the agent for stabilizing lactoferrin against heat treatment according to any one of the above (31) to (40) to lactoferrin; and heat-sterilizing the thermally-stabilized lactoferrin.

The effect of the agent for stabilizing lactoferrin against heat treatment according to the present invention on stabilization of lactoferrin against heat treatment is exerted not only on isolated lactoferrin but also on lactoferrin contained in a composition including lactoferrin and one or more other components. Therefore, the above-described method for stabilizing lactoferrin against heat treatment includes a method for stabilizing a lactoferrin-containing composition against heat treatment and the above-described method for heat-sterilizing lactoferrin includes a method for heat-sterilizing a lactoferrin-containing composition.

Effects of the Invention

The agent according to the first or second aspect of the present invention can contribute heat-stability to lactoferrin at a pH ranging from slightly acidic to slightly alkaline, more specifically at a pH ranging from 6 to 9. Therefore, the use of the agent according to the first or second aspect of the present invention makes it possible to sterilize various protein-containing products such as foods, beverages, feeds, and pharmaceutical products in the above-described pH range without affecting the physical properties and functions of lactoferrin. For example, the agent according to the first or second aspect of the present invention is suitable for use in foods and beverages, which undergo heating during production, such as jellies, puddings, ice creams, yoghurts, juice drinks, milk drinks, sports drinks, soups, baked foods, powdered milk, infant formula, and liquid diets.

The composition according to the third or fourth aspect of the present invention exerts its effect even when the amount of a nucleic acid used or the total amount of a nucleic acid and a metal used is much smaller than the amount of lactoferrin. Therefore, the composition including a nucleic acid and lactoferrin according to the present invention or the composition including a nucleic acid, a metal, and lactoferrin according to the present invention can be added to various products such as foods, beverages, feeds, and pharmaceutical products without affecting the composition and physical properties of such products.

The pharmaceutical products according to the fifth aspect of the present invention, the food or beverage according to the sixth aspect of the present invention, and the feed according to the seventh aspect of the present invention do not undergo denaturation of lactoferrin, thereby making it possible to effectively ingest lactoferrin.

The method for heat-sterilizing lactoferrin according to the eighth aspect or ninth aspect of the present invention makes it possible to heat-sterilize lactoferrin without denaturing it.

The present invention also includes embodiments using a metal. In the case of using a metal, the effect of the present invention can be obtained even when the amount of a metal used is very small, and therefore there is no fear that a metallic smell will be caused. For this reason, the embodiments according to the present invention using a metal can be applied without any problem to cases where addition of a metal is undesirable.

Further, the utilization of a soft roe-derived nucleic acid used in the present invention can be proposed also as a method for effectively utilizing soft roe. This is because soft roe has been heretofore mostly disposed of.

As described above, according to the present invention, it is possible to stabilize lactoferrin against heat treatment. This makes it possible to minimize the deactivation of lactoferrin when the lactoferrin is subjected to heat sterilization. Therefore, according to the present invention, lactoferrin can be heat-sterilized without the necessary of performing a complicated process such as a process in which pH is once adjusted to a value in the acid region before heat sterilization and is then again adjusted to a value in the neutral region and without the necessity of adding a stabilizer in such a large amount that the physical properties of lactoferrin are affected.

Heretofore, it has been difficult to add lactoferrin to products such as puddings and jellies because their production processes absolutely require heating. However, according to the present invention, it is possible to add lactoferrin to such products to satisfactorily exhibit its activities. There has been a strong demand for products such as puddings and jellies containing lactoferrin in the fields of childcare and nursing care, because they are easy to swallow and are therefore suitable for infants and aged persons having difficulty in swallowing and lactoferrin has various activities and is therefore particularly beneficial to infants and aged persons having a delicate constitution. According to the present invention, it is possible to appropriately produce lactoferrin-containing products which have been difficult to produce.

BEST MODE FOR CARRYING OUT THE INVENTION

Hereinbelow, preferred embodiments of the present invention will be described in detail. However, the present invention is not limited to the following preferred embodiments, and various changes may be made without departing from the scope of the invention. It is to be noted that in this specification, percentages (%) are expressed in mass (mg)/volume (mL) unless otherwise specified. However, since the specific gravity of purified water used as a solvent for preparation of samples is around 1, percentages may also be expressed as weight-percent concentration (mass (mg)/mass (mg)).

[Heat-Stability (Thermal Stability)]

In the present invention, lactoferrin having improved "heat-stability" means lactoferrin that can keep its unique three-dimensional structure or does not lose its various physiological activities even after exposed to heat. It is to be noted that "heat-stability" can also be expressed as "thermal stability".

More specifically, in the present invention, "heat-stability" of lactoferrin can be evaluated by measuring the unsaturated iron binding capacity of lactoferrin.

As other indicators of heat-stability of lactoferrin from the viewpoint of retention of structure, the molecular weight of lactoferrin and the presence or absence of aggregation and/or precipitation of lactoferrin can be mentioned. More specifically, "heat-stability" of lactoferrin can be evaluated also by measuring the molecular weight of lactoferrin by SDS-PAGE or by visually observing the presence or absence of aggregation and/or precipitation of lactoferrin.

Further, in the present invention, "heat-stability" can also be evaluated by the percentage of residual lactoferrin determined by measuring a lactoferrin content before and after heating by a latex agglutination test based on antigen-antibody reaction. In the present invention, the percentage of residual lactoferrin can be defined as follows.

Percentage of residual lactoferrin (%)=(lactoferrin content after heating/lactoferrin content before heating)×100

When the percentages of residual lactoferrin of lactoferrin-containing products such as foods and beverages are 20% or higher, the activities of lactoferrin are satisfactorily exhibited. Therefore, the percentage of residual lactoferrin is preferably 20% or higher, more preferably 25% or higher, even more preferably 30% or higher, even more preferably 35% or higher.

[Nucleic Acid]

In the present invention, a nucleic acid contributing heat-stability to lactoferrin refers to DNA (deoxyribonucleic acid), RNA (ribonucleic acid), or a mixture thereof. The DNA or RNA may be either double-stranded or single-stranded. According to a preferred embodiment of the present invention, the nucleic acid has a molecular weight in the range of 5 kDa to 12,000 kDa, preferably in the range of 60 kDa to 1200 kDa.

The nucleic acid to be used in the present invention may be one chemically synthesized by a conventional method or one extracted from a natural source such as animals (e.g., human beings, bovines, mice, and fishes), plants, and bacteria. Particularly preferred examples of such a nucleic acid derived from a natural source include nucleic acids extracted from soft roe (milt) of fishes such as salmons, herrings, trouts, and cods. As the nucleic acid, a nucleic acid and/or a salt thereof can be used. Examples of the salt include sodium salts and potassium salts.

In the present invention, various nucleic acid reagents can be used as nucleic acids. The nucleic acid reagents may contain a nucleic acid and/or a salt thereof. The nucleic acid content of such a reagent is preferably in the range of 60 to 100%, more preferably in the range of 80 to 100%, particularly preferably in the range of 90 to 100%.

Here, the purity of DNA contained in a nucleic acid reagent can be determined by measuring the absorbance of a solution obtained by dissolving 100 mg of a reagent containing DNA in 100 mL of purified water with the use of a spectrophotometer (manufactured by Nanodrop Technologies under the trade name of "Nanoprop ND-1000") at 260 nm.

The nucleic acid reagent may further contain an inorganic salt in addition to a nucleic acid and/or a salt thereof. The salt contained in the nucleic acid reagent is not particularly limited as long as it is a salt generally used. Examples of such a salt include sodium salts, potassium salts, calcium salts, magnesium salts, ammonium salts, and pyridinium salts.

[Lactoferrin]

Lactoferrin to be stabilized against heat treatment according to the present invention is not particularly limited, and examples of lactoferrin usable in the present invention include: commercially-available lactoferrin; lactoferrin separated from colostrum, transitional milk, normal milk, or late lactation milk of mammals (e.g., human beings, bovines, water buffaloes, horses, goats, and sheep), skimmed milk as a processed product of such milk, or whey by a conventional method such as ion-exchange chromatography; apo-lactoferrin obtained by removing iron from lactoferrin by a conventional method; and partial metal-binding lactoferrin or metal-saturated lactoferrin obtained by partially or fully chelating apo-lactoferrin with a metal such as iron, copper, zinc, or manganese.

Further, human lactoferrin or the like produced by transgenic fungi, transgenic cows, or the like obtained by genetic recombination technology can also be used in the present invention.

Other examples of lactoferrin to be stabilized against heat treatment according to the present invention include various lactoferrin reagents. The purity of the lactoferrin reagent, that is, the lactoferrin content of the lactoferrin reagent is preferably in the range of 30 to 100%, more preferably in the range of 70 to 100%, particularly preferably in the range of 85 to 100%.

Lactoferrin purity can be calculated by, for example, the following formula.

$$\text{Lactoferrin purity (\%)} = \text{total protein content} \times \text{ratio of lactoferrin to total protein}$$

[Metal]

Examples of a metal usable in the present invention include various metals and salts thereof. More specifically, metals such as iron, copper, zinc, manganese, cobalt, nickel, and aluminum and salts thereof can be used. According to a preferred embodiment of the present invention, specific examples of a usable metal include ferric sulfate, copper sulfate, zinc sulfate, manganese sulfate, nickel sulfate, and aluminum sulfate, and chlorides, phosphates, and gluconates of these metals. Among metals, iron, copper, and zinc are preferred, and copper is most preferred.

It is to be noted that other examples of a metal usable in the present invention include various metal reagents. The metal reagent may include a metal and/or a salt thereof. Examples of such a metal reagent include metal salts.

[Agent (Agent for Stabilizing against Heat Treatment)]

An agent according to a first aspect of the present invention and an agent according to a second aspect of the present invention can contribute heat-stability to lactoferrin and inhibit denaturation of lactoferrin during heat sterilization, and are therefore suitable for use together with lactoferrin. Further, these agents are also suitable for use in, for example, lactoferrin-containing pharmaceutical products, foods, beverages, and feeds because they can contribute heat-stability to lactoferrin during heat sterilization so that the structure and activities of lactoferrin are maintained even after heating. Therefore, the agent for stabilizing against heat treatment according to the present invention can be used in such a manner as described above. The agent (agent for stabilizing against heat treatment) according to the present invention may also be used as an agent for sterilization and a heat-stabilizing agent for pasteurization.

[pH]

According to a preferred embodiment of the present invention, it is possible to improve thermal stability of lactoferrin, that is, to contribute heat-stability to lactoferrin with the use of a nucleic acid or a nucleic aid and a metal in a pH range from slightly acidic to alkaline, in which lactoferrin is unstable to heat, preferably in a pH range from 6 to 10, more preferably in a pH range from 6 to 9, particularly preferably in a pH range from 6 to 8.

The agent (agent for stabilizing against heat treatment) including a nucleic acid as an active ingredient or the agent (agent for stabilizing against heat treatment) including a nucleic acid and a metal as active ingredients according to the present invention can contribute heat-stability to lactoferrin in the above-mentioned pH range from 6 to 10. Therefore, unlike conventional methods, it is not necessary to previously adjust the pH of lactoferrin to a value lower than neutral, that is, to a value in the acidic region before heat sterilization. In addition, there is also an advantage that it becomes possible to easily sterilize lactoferrin even in a pH range from neutral to alkaline by adding a nucleic acid or a nucleic acid and a metal to lactoferrin. Namely, the present invention makes it possible to perform heat treatment which has been hitherto impossible, thereby improving the effect of sterilizing lactoferrin and the effect of assisting the sterilization of lactoferrin in the pH range of 6 to 9.

As described above, the agent for contributing heat-stability (agent for stabilizing against heat treatment) according to the present invention including a nucleic acid as an active ingredient has the effect of contributing heat-stability to lactoferrin in the alkaline region in which lactoferrin is conventionally unstable to heat, thereby making it possible to provide a novel method for heat-sterilizing lactoferrin. In addition, it is also possible to heat-sterilize lactoferrin-containing products such as pharmaceutical products, foods, and feeds, which are preferably prepared in a pH range from neutral to alkaline, without pH adjustment by adding the agent according to the present invention to these products.

In order to allow the pH of lactoferrin to reliably lie within the above-described preferred pH range, the agent for stabilizing against heat treatment according to the present invention may contain a pH adjusting component. Such a pH adjusting component is not particularly limited as long as it has the pH buffering ability to keep the pH of lactoferrin within the above-described preferred pH range during heat treatment. For example, organic acids and/or organic acid salts can be used. More specifically, a mixture of at least one acid selected from the group consisting of commercially-available food additives such as citric acid, lactic acid, malic acid, succinic acid, tartaric acid, glutamic acid, and alginic acid and at least one salt selected from the group consisting of citrates (e.g., trisodium citrate and tripotassium citrate), lactates (e.g., sodium lactate), malates (e.g., sodium malate), succinates (e.g., monosodium succinate and disodium succinate), tartrates (e.g., sodium tartrate and potassium hydrogen tartrate), glutamates (e.g., sodium glutamate and potassium glutamate), and arginic acid salts (e.g., arginine hydrochloride) can be used. All these salts are widely used as food additives and pharmaceutical ingredients and are easily available in the market.

[Effective Amount]

According to the present invention, the mass ratio between the amount of lactoferrin and the effective amount of a nucleic acid added to contribute heat-stability to lactoferrin (i.e., to stabilize lactoferrin against heat treatment) is preferably 1:0.09 to 6.3, 1:0.1 to 6.0, 1:0.10 to 5.7, 1:0.09 to 4.2, 1:0.09 to 2.1, or 1:0.09 to 1.0, more preferably 1:1.0.

According to a preferred embodiment of the present invention, the mass ratio between the amount of lactoferrin and the amount of a nucleic acid added is 1:0.19 to 6.3, preferably 1:0.2 to 6.0 or 1:0.21 to 5.7, or is 1:0.28 to 6.3, preferably 1:0.3 to 6.0 or 1:0.31 to 5.7, or is 1:0.38 to 6.3, preferably 1:0.4 to 6.0 or 1:0.42 to 5.7, or is 1:0.47 to 6.3, preferably 1:0.5 to 6.0 or 1:0.52 to 5.7, or is 1:0.9 to 6.3, preferably 1:1 to 6.0 or 1:1 to 5.7, or is 1:1.9 to 6.3, preferably 1:2.0 to 6.0 or 1:2.1 to 5.7, or is 1:3.8 to 6.3, preferably 1:4.0 to 6.0, more preferably 1:4.2 to 5.7.

Particularly, when the pH of lactoferrin is in the range of 6 to 9, the mass ratio between lactoferrin and a nucleic acid added is preferably 1:0.19 to 4.2, more preferably 1:0.21 to 3.8.

The molar ratio between the amount of lactoferrin and the effective amount of a metal added to contribute heat-stability to lactoferrin is preferably 1:0.04 to 3, more preferably 1:0.04 to 2, even more preferably 1:0.04 to 1, even more preferably 1:0.04 to 0.5, even more preferably 1:0.04 to 0.4, even more preferably 1:0.04 to 0.3, even more preferably 1:0.04 to 0.2, even more preferably 1:0.04 to 0.1, most preferably 1:0.04 to 0.09.

Therefore, when a nucleic acid is used for the purpose of preventing lactoferrin from thermally denatured by heat sterilization in the production processes of lactoferrin-containing compositions, more specifically, in the production processes of lactoferrin-containing pharmaceutical products, foods, and feeds, the mass ratio between lactoferrin and the nucleic acid added is preferably 1:0.09 to 6.3.

This makes it possible to produce a pharmaceutical product, food, or feed containing a heat-stabilized composition including a nucleic acid and lactoferrin.

Further, when a nucleic acid and a metal are used for the purpose of preventing lactoferrin from thermally denatured by heat sterilization in the production processes of lactoferrin-containing compositions, more specifically, in the production processes of lactoferrin-containing pharmaceutical products, foods, and feeds, the mass ratio between lactoferrin and the nucleic acid added is preferably 1:0.09 to 6.3 and the mass ratio between lactoferrin and the metal added is preferably 1:0.04 to 3.

This makes it possible to produce a pharmaceutical product, food, or feed containing a heat-stabilized composition including a nucleic acid, a metal, and lactoferrin.

[Composition]

A composition according to a third aspect of the present invention includes a nucleic acid and lactoferrin in a mass ratio of nucleic acid to lactoferrin of 0.09 to 6.3.

A nucleic acid reagent to be used as a nucleic acid in the present invention may be DNA, RNA, a mixture thereof, or a mixture of any one of them and a salt.

A lactoferrin reagent to be used as lactoferrin in the present invention may be human lactoferrin, bovine lactoferrin, a mixture thereof or a mixture of any one of them and a salt.

A composition according to a fourth aspect of the present invention includes a nucleic acid, a metal, and lactoferrin, wherein a mass ratio of the nucleic acid to the lactoferrin is 0.09 to 6.3 and a molar ratio of the metal to the lactoferrin is 0.04 to 3.0.

A nucleic acid to be used in the composition according to the fourth aspect of the present invention is not particularly limited as long as it is a nucleic acid reagent usable in the agent according to the present invention. As described above, the mass ratio between the amount of lactoferrin and the effective amount of a nucleic acid added to contribute heat-stability to lactoferrin is preferably 1:0.09 to 6.3, more preferably 1:0.09 to 4.2, even more preferably 1:0.09 to 2.1, even more preferably 1:0.09 to 1.0, preferably 1:1.0.

A metal to be used in the composition according to the fourth aspect of the present invention is not particularly limited as long as it is a metal reagent usable in the agent according to the present invention. The molar ratio between the amount of lactoferrin and the effective amount of a metal added to contribute heat-stability to lactoferrin is preferably 1:0.04 to 3, more preferably 1:0.04 to 2, even more preferably 1:0.04 to 1, even more preferably 1:0.04 to 0.5, preferably 1:0.04 to 0.09.

Lactoferrin to be used in the composition according to the present invention is not particularly limited as long as it is a lactoferrin reagent usable in the agent according to the present invention, but is preferably one not yet denatured by heating or sterilization. This is because the effect of the present invention is exhibited when lactoferrin is heated in the form of a composition including lactoferrin, a nucleic acid, and a metal.

[Pharmaceutical Product]

A fifth aspect of the present invention provides a pharmaceutical product containing the composition according to the present invention. The pharmaceutical product can be prepared as formulations in various dosage forms by well-known methods. According to a preferred embodiment of the fifth aspect of the present invention, the pharmaceutical product is prepared as orally-administered formulations. In a case where the pharmaceutical product is prepared as formulations, a nucleic acid and lactoferrin are used in a mixed state or a nucleic acid, a metal, and lactoferrin are used in a mixed state.

The pharmaceutical product according to the fifth aspect of the present invention can be prepared as a formulation by, for example, adding a pharmaceutically-acceptable additive such as an excipient to a nucleic acid and lactoferrin or to a nucleic acid, a metal, and lactoferrin. In a case where the pharmaceutical product according to the fifth aspect of the present invention is prepared as a formulation, the lactoferrin content of the formulation is not particularly limited. It is considered that a nucleic acid and lactoferrin basically have little side effect, but the nucleic acid content of the formulation is generally 0.01 to 60% by mass, preferably 1 to 30% by mass, the lactoferrin content of the formulation is generally 0.1 to 60% by mass, preferably 10 to 50% by mass, and the metal content of the formulation is generally 0 to $1\times10^{-2}$% by mass, preferably 0 to $1\times10^{-2}$% by mass or generally $1\times10^{-8}$ to $1\times10^{-2}$% by mass, preferably $1\times10^{-8}$ to $1\times10^{-2}$% by mass.

In a case where the pharmaceutical product according to the fifth aspect of the present invention is prepared as a formulation, various additives such as excipients, binders, disintegrants, lubricants, stabilizers, flavoring agents, diluents, and injection solvents can be used. Specific examples of the formulation include tablets (including sugarcoated tablets, enteric-coated tablets, and buccal tablets), powders, capsules (including enteric-coated capsules and soft capsules), granules (including coated granules), pills, troches, encapsulated-liposome agents, liquids, and their pharmaceutically-acceptable sustained-release preparations.

Examples of carriers and excipients to be used in these formulations include lactose, glucose, saccharose, mannitol, potato starch, corn starch, calcium carbonate, calcium phosphate, calcium sulfate, crystalline cellulose, licorice powder, and gentiana powder. Examples of binders include starch, gelatin, syrup, polyvinyl alcohol, polyvinyl ether, polyvinyl pyrrolidone, hydroxypropyl cellulose, ethyl cellulose, methyl cellulose, and carboxymethyl cellulose.

Examples of disintegrants include starch, agar, gelatin powder, sodium carboxylmethylcellulose, calcium carboxymethylcellulose, crystalline cellulose, calcium carbonate, sodium hydrogen carbonate, and sodium alginate.

Examples of lubricants include magnesium stearate, hydrogenated vegetable oils, and macrogol. Examples of colorants include Red No. 2, Yellow No. 4, and Blue No. 1 which are allowed to be added to pharmaceutical products.

If necessary, tablets and granules may be coated with saccharose, hydroxypropyl cellulose, purified shellac, gelatin, sorbitol, glycerin, ethyl cellulose, hydroxypropyl cellulose, hydroxypropylmethyl cellulose, polyvinyl pyrrolidone, cellulose phthalate acetate, hydroxypropylmethyl cellulose phthalate, methyl methacrylate, and methacrylic acid polymers.

Further, a pharmaceutical composition to be used in combination may be contained as an active ingredient in the agent according to the present invention or may be prepared as a separate agent and sold in combination with the agent according to the present invention.

[Foods and Beverages]

Examples of foods and beverages containing the composition according to the present invention include foods and beverages produced by, for example, blending a nucleic acid according to the present invention and lactoferrin in the form of powder or aqueous solution (e.g., syrup) with soft drinks, milk drinks, or concentrated stock solutions and conditioning powders of these drinks; milk products such as processed milk and fermented milk; enteral nutritional foods; powdered modified milk products and liquid modified milk products; and functional foods. Other examples of such foods and beverages include drinks such as carbonated drinks, energy drinks, and fruit drinks (including concentrated stock solutions and conditioning powders of these drinks); frozen desserts such as ice creams, sorbets, and ice shavings topped with syrups; noodles such as Japanese noodles of buckwheat, Japanese noodles of wheat, bean-starch noodles, pasta-wrappings for Chinese stuffed dumplings, pasta-wrappings for Chinese steamed dumplings, Chinese noodles, and instant noodles; confectionery such as drops, chewing gums, candies, gums, chocolates, tablets, snack foods, biscuits, jellies, jams, creams, and baked goods; processed fish or meat products such as Japanese steamed fish pastes, hams, and sausages; fats and oils and oil processed foods such as salad oils, frying oils, margarine, mayonnaise, shortening, whipped cream, and dressing; seasonings such as sauces; and soups, stews, salads, prepared foods, pickles, and breads.

These foods and beverages can be produced by, for example, blending lactoferrin (including lactoferrin in the form of powder or aqueous solution (e.g., syrup)) with a nucleic acid and sugars such as dextrin and starch; proteins such as gelatin, soybean protein, and corn protein; amino acids such as alanine, glutamine, arginine, and isoleucine; polysaccharides such as cellulose and gum Arabic; and fats and oils such as soybean oils and medium-chain fatty acid triglycerides.

Preferred examples of the form of these foods and beverages include supplements in liquid or tablet form.

[Feeds]

A feed containing the composition according to the present invention is not particularly limited as long as it contains a nucleic acid and lactoferrin or contains a nucleic acid, a metal, and lactoferrin. Such a feed can be produced by, for example, blending lactoferrin with grains such as corn, wheat, barley, rye, and milo; vegetable oil meals such as soybean oil meal, rapeseed oil meal, coconut oil meal, and linseed oil meal; brans such as wheat bran, barley bran, rice bran, and defatted rice bran; by-products of food production such as corn gluten meal and corn germ meal; animal-derived feeds such as fish meal, powdered skim milk, whey, yellow grease, and tallow; yeasts such as torula yeast and beer yeast; mineral feeds such as calcium tertiary phosphate and calcium carbonate; fats and oils; free-form amino acids; and sugars. Examples of the feed include pet foods, livestock foods, and fish feeds.

Test methods used in Test Examples of the present invention are as follows.

More specifically, in the present invention, the following indicators (i.e., unsaturated iron binding capacity (UIBC) of lactoferrin, SDS electrolysis, latex agglutination test, and visual observation of aggregation and/or precipitation reaction) were used to evaluate the heat-stability of lactoferrin.

[Unsaturated Iron Binding Capacity (UIBC)]

The ability of a lactoferrin molecule to form a chelate with iron molecules, that is, so-called iron binding capacity is well known as one of physiological functions of lactoferrin, and then demonstrates that undenatured lactoferrin is present (see, for example, Japanese Patent No. 2835902).

A test method is as follows. A known excess amount of iron is added to a sample to saturate free lactoferrin, and then the amount of residual iron measured by a reducing-coloring reagent is subtracted from the known amount of excess iron added to determine unsaturated iron binding capacity. Unsaturated iron binding capacity (UIBC) can be measured by using, for example, a commercially-available measuring kit such as an unsaturated iron binding capacity kit (manufactured by Nitto Boseki Co., Ltd. under the trade name of N-TEST UIBC).

The unsaturated iron binding capacity of lactoferrin was measured in the following manner. One milliliter of iron (III) ammonium sulfate was placed as an iron reagent in a test tube, and then 0.2 mL of a sample was added to the iron reagent. The iron reagent and the sample were mixed well, and then the mixture was left standing at room temperature for 5 minutes. Then, 1 mL of 2-nitroso-5-(N-propyl-N-sulphopropylamino)phenol (Nitroso-PSAP) as a reducing-coloring reagent was added to and mixed well with the mixture contained in the test tube to obtain a specimen, and the absorbance of the specimen was measured at 760 nm. The absorbance of purified water as a control was also measured at 760 nm. UIBC was determined by the following formula.

$$\text{UIBC}(\mu g/dL) = (ARb - AS)/ARb \times 500$$

ARb: absorbance of reagent blank

AS: absorbance of specimen

It is to be noted that in the present invention, when the UIBC of lactoferrin measured before heating is defined as 100%, the UIBC of the lactoferrin measured after heating is preferably 10 to 100%, particularly preferably 30 to 100%. Therefore, in the present invention, when the UIBC of lactoferrin measured after heating lies within the above preferred range, the "heat-stability" of the lactoferrin is evaluated as good.

[SDS-PAGE]

Heated lactoferrin was subjected to SDS-PAGE. After the completion of electrophoresis, the band pattern of the lactoferrin was analyzed to determine the presence or absence of a band corresponding to lactoferrin according to the following criteria. Based on the result of SDS-PAGE, the heat-stability of the lactoferrin was evaluated. When the result of SDS-PAGE was "○" or "Δ", "heat-stability" was evaluated as "good".

○: A band corresponding to lactoferrin was observed.

Δ: A band corresponding to lactoferrin was barely observed.

x: No band corresponding to lactoferrin was observed.

[Latex Agglutination Test]

In the Test Examples of the present invention, the lactoferrin content of a sample was measured by a latex agglutination test as an indicator for evaluating the heat-stability of lactoferrin.

In the present invention, the latex agglutination test is performed by latex agglutination turbidimetry using an anti-lactoferrin antibody (rabbit)-sensitized latex. In the latex agglutination test, latex particles coated with anti-lactoferrin antibody are used, and therefore lactoferrin contained in a sample causes an antigen-antibody reaction with the anti-lactoferrin antibody immobilized on the latex particles and then agglutination occurs. A change in absorbance caused by the occurrence of agglutination is measured at a constant wavelength. Then, the lactoferrin content of the sample is determined based on the measurement result. It is to be noted that the lactoferrin content of the sample is measured before and after the heating of the sample.

A preferred example of a method for measuring lactoferrin by a latex agglutination test includes a method using a commercially-available kit (manufactured by FUJITEX Co., Ltd. under the trade name of "LACTOFERRIN LATEX TEST, BOVINE").

[Visual Observation of Aggregation and/or Precipitation Reaction]

The presence or absence of aggregation and/or precipitation of lactoferrin was visually observed after heating and evaluated according to the following criteria.

−: No aggregation and no precipitation were observed in a sample and the sample was transparent.

±: No aggregation and no precipitation were observed in a sample but the sample turned white with turbidity.

+: Aggregation and/or precipitation were observed in a sample.

EXAMPLES

Hereinbelow, the present invention will be described in detail with reference to the following examples, but is not limited thereto.

Test Example 1

Test Example 1 was performed to examine the relationship between pH ranging from slightly acidic to alkaline and temperature from the viewpoint of the effect of a nucleic acid on contributing heat-stability to lactoferrin.

(1) Preparation of Samples 100 mg of a nucleic acid reagent (manufactured by Nissei Bio Co., Ltd. under the trade name of "DNA-NA SALT") as a nucleic acid and 100 mg of a lactoferrin reagent (manufactured by Milei GmbH under the trade name of "MLF-1") as lactoferrin were dissolved in 100 mL of purified water to prepare a test sample. On the other hand, 100 mg of a lactoferrin reagent (manufactured by Milei GmbH under the trade name of "MLF-1") was dissolved in 100 mL of purified water to prepare a solution as a control sample.

The "DNA-NA SALT" (manufactured by Nissei Bio Co., Ltd.) used in the Test Example 1 as a nucleic acid reagent is a high-molecular weight DNA concentration derived from salmon soft roe, and has a DNA content of 90% or higher. The number of base pairs of the "DNA-NA SALT" determined by electrophoresis was 100 to 2000. From the result, the molecular weight of the "DNA-NA SALT" was calculated as 60 to 1200 kpa.

The lactoferrin purity of the lactoferrin reagent was determined in the following manner. The protein concentration of the lactoferrin reagent was measured by the Kjeldahl method, and the ratio of lactoferrin to total protein was measured by high performance liquid chromatography. From the measurement results, the lactoferrin purity of the lactoferrin reagent was calculated by the above-described method and was found to be 95.3% (total protein content: 97.8%, ratio of lactoferrin to total protein: 97.40). Hereinafter, the lactoferrin purity of the lactoferrin reagent is 95.3% unless otherwise specified.

The test sample and the control sample were each adjusted to pH 6, 7, 8, 9, 10, 11, and 12 by adding a 0.1 N hydrochloric acid solution or a 0.1 N sodium hydroxide solution. In this way, the test samples adjusted to pH 6 to 12 and the control samples adjusted to pH 6 to 12 were prepared.

(2) Test Method 4 mL aliquots of each of the samples were dispensed into glass tubes and subjected to heat treatment at 80, 90, 100, 110, and 120° C. for 5 minutes. It is to be noted that heating at 80° C. and 90° C. was performed using a water bath (manufactured by HAAKE) and heating at 100, 110, and 120° C. was performed using an autoclave (manufactured by TOMY). After the completion of the heat treatment, the samples were visually observed to determine the presence or absence of aggregation and/or precipitation of lactoferrin and evaluated according to the following criteria.

−: No aggregation and no precipitation were observed in a sample and the sample was transparent.

±: No aggregation and no precipitation were observed in a sample but the sample turned white with turbidity.

+: Aggregation and/or precipitation were observed in a sample.

Further, as another indicator for evaluating the heat-stability of lactoferrin, SDS-PAGE was performed using LabChip automated electrophoresis system EXPERION (trademark) (manufactured by Bio-Rad Laboratories) and the band pattern of lactoferrin obtained by SDS-PAGE was analyzed according to the following criteria.

More specifically, the heated lactoferrin samples were subjected to SDS-PAGE. After the completion of SDS-PAGE, the band pattern of lactoferrin was analyzed to determine the presence or absence of a band corresponding to lactoferrin. Based on the result, the heat-stability of lactoferrin was evaluated according to the following criteria.

○: A band corresponding to lactoferrin was observed.

Δ: A band corresponding to lactoferrin was barely observed.

x: No band corresponding to lactoferrin was observed.

(3) Test Results

The results of the Test Example 1 are shown in Tables 1 and 2. Table 1 shows the evaluation result of heat-stability of lactoferrin contained in each of the mixed solutions of lactoferrin and a nucleic acid (i.e., test samples), and Table 2 shows the evaluation result of heat-stability of lactoferrin contained in each of the solutions containing only lactoferrin (i.e., control samples).

As can be seen from Table 2, in the cases of the solutions containing only lactoferrin (i.e., control samples) heated to 90° C. or higher, a band corresponding to lactoferrin was not observed in a band pattern obtained by SDS-PAGE at some pH values. Further, white turbidity or aggregation and/or precipitation of lactoferrin were observed in the pH range of 7 to 9 even when the heat treatment was performed at 80° C. This indicates that the heat-stability of lactoferrin contained in each of the control samples adjusted to pH 7 to 9 was reduced.

On the other hand, as can be seen from Table 1, in all the cases of the mixed solutions of lactoferrin and a nucleic acid (i.e., test samples) heated to 80 to 120° C., a band corresponding to lactoferrin was observed in a band pattern obtained by SDS-PAGE in the pH range of 6 to 10.

Further, all the mixed solutions of lactoferrin and a nucleic acid adjusted to pH 6 to 12 were transparent even after heating to 80 to 120° C. and no aggregation and no precipitation of lactoferrin were observed.

From the results, it was found that the heat-stability of lactoferrin was maintained by a nucleic acid in the pH range of 6 to 12.

TABLE 1

Mixed Solutions of Lactoferrin and Nucleic Acid (Test Samples)

| Temperature (° C.) | Test Items | pH 6 | 7 | 8 | 9 | 10 | 11 | 12 |
|---|---|---|---|---|---|---|---|---|
| 80 | Visual Observation | − | − | − | − | − | − | − |
|  | SDS-PAGE | ○ | ○ | ○ | ○ | ○ | X | X |
| 90 | Visual Observation | − | − | − | − | − | − | − |
|  | SDS-PAGE | ○ | ○ | ○ | ○ | ○ | X | X |
| 100 | Visual Observation | − | − | − | − | − | − | − |
|  | SDS-PAGE | ○ | ○ | ○ | ○ | ○ | X | X |
| 110 | Visual Observation | − | − | − | − | − | − | − |
|  | SDS-PAGE | ○ | ○ | ○ | ○ | ○ | X | X |
| 120 | Visual Observation | − | − | − | − | − | − | − |
|  | SDS-PAGE | ○ | ○ | ○ | ○ | Δ | X | X |

TABLE 2

Lactoferrin Solutions (Control Samples)

| Temperature (° C.) | Test Items | pH 6 | 7 | 8 | 9 | 10 | 11 | 12 |
|---|---|---|---|---|---|---|---|---|
| 80 | Visual Observation | − | ± | ± | + | − | − | − |
|  | SDS-PAGE | ○ | ○ | ○ | Δ | Δ | ○ | X |
| 90 | Visual Observation | − | ± | ± | + | − | − | − |
|  | SDS-PAGE | ○ | ○ | Δ | X | X | ○ | X |
| 100 | Visual Observation | − | ± | + | + | − | − | − |
|  | SDS-PAGE | ○ | X | X | X | X | ○ | X |
| 110 | Visual Observation | ± | + | + | + | − | − | − |
|  | SDS-PAGE | Δ | X | X | X | X | Δ | X |
| 120 | Visual Observation | ± | + | + | + | − | − | − |
|  | SDS-PAGE | Δ | X | X | X | X | X | X |

(Evaluation Criteria for Visual Observation)

−: No aggregation and no precipitation were observed in a sample and the sample was transparent.

±: No aggregation and no precipitation were observed in a sample but the sample turned white with turbidity.

+: Aggregation and/or precipitation were observed in a sample.

(Evaluation Criteria for SDS-Page)

○: A band corresponding to lactoferrin was observed.

Δ: A band corresponding to lactoferrin was barely observed.

x: No band corresponding to lactoferrin was observed.

Test Example 2

Test Example 2 was performed to examine the mixing ratio between a nucleic acid and lactoferrin from the viewpoint of the effect of a nucleic acid on contributing heat-stability to lactoferrin.

(1) Preparation of Samples

Samples were prepared by adding a nucleic acid reagent and a lactoferrin reagent to purified water so that the mass ratios of the nucleic acid reagent to the lactoferrin reagent were 0, 0.1, 0.2, 0.3, 0.4, 0.5, 1, 2, 4, and 6. It is to be noted that the nucleic acid reagent and the lactoferrin reagent used in the Test Example 2 were the same as those used in the Test Example 1.

Further, aliquots of each of the samples were adjusted to pH 6, 7, 8, and 9 by adding a 0.1 N hydrochloric acid solution or a 0.1 N sodium hydroxide solution to prepare test samples.

(2) Test Method

Each of the test samples was subjected to heat treatment by heating at 80° C. for 5 minutes in a water bath (manufactured by HAAKE).

After the completion of the heat treatment, the unsaturated iron binding capacity (UIBC) of lactoferrin contained in the test sample was determined in the following manner.

The unsaturated iron binding capacity (UIBC) of lactoferrin was determined using an unsaturated iron binding capacity kit (manufactured by Nitto Boseki Co., Ltd. under the trade name of N-TEST UIBC).

First, 1 mL of iron (III) ammonium sulfate was placed as an iron reagent in a test tube, and then 0.2 mL of the test sample was added to the iron reagent. The iron reagent and the test sample were mixed well, and then the mixture was left standing at room temperature for 5 minutes. Then, 1 mL of 2-nitroso-5-(N-propyl-N-sulphopropylamino)-phenol (Nitroso-PSAP) as a reducing-coloring reagent was added to and mixed well with the mixture contained in the test tube to obtain a specimen, and the absorbance of the specimen was measured at 760 nm. The absorbance of purified water as a control was also measured at 760 nm. The unsaturated iron binding capacity of lactoferrin contained in the test sample was calculated from the measurement values of absorbance.

(3) Test Results

The results of the Test Example 2 are shown in Tables 3 to 6. Table 3 shows the evaluation result of heat-stability of lactoferrin contained in each of the test samples having different mass ratios of nucleic acid reagent to lactoferrin reagent at pH 6. Likewise, Table 4 shows the evaluation result of heat-stability of lactoferrin at pH 7, Table 5 shows the evaluation result of heat-stability of lactoferrin at pH 8, and Table 6 shows the evaluation result of heat-stability of lactoferrin at pH 9. It is to be noted that in the Tables 3 to 6, "nucleic acid/lactoferrin" means the mixing ratio between the nucleic acid reagent and the lactoferrin reagent used in the Test Example 2.

As can be seen from the results shown in Tables 3 to 6, in all the cases of the test samples adjusted to pH 6 to 9, the unsaturated iron binding capacity (UIBC) of lactoferrin under conditions where a nucleic acid and lactoferrin were both present (i.e., the mass ratio of the nucleic acid reagent to the lactoferrin reagent was 0.1 to 6) was higher than that of lactoferrin under conditions where only lactoferrin was present. This indicates that the heat-stability of lactoferrin is improved under conditions where a nucleic acid and lactoferrin are both present.

Particularly, as can be seen from Tables 3 to 6, the unsaturated iron binding capacity (UIBC) of lactoferrin was higher than 50% when the mass ratio of the nucleic acid reagent to the lactoferrin reagent was in the range of 0.2 to 2.

From the results of the Test Example 2, it has become apparent that the effect of a nucleic acid on contributing heat-stability to lactoferrin is effectively exhibited when the mass ratio of the nucleic acid reagent to the lactoferrin reagent is in the range of 0.1 to 6.

Here, the purity of the nucleic acid reagent used in the Test Example 2 was 90 to 100% and the purity of the lactoferrin reagent used in the Test Example 2 was measured as 95.3%. Therefore, when the purity of the nucleic acid reagent is 100%, a minimum value of the mass ratio of the nucleic acid reagent to the lactoferrin reagent of 0.1 corresponds to a minimum value of the mass ratio of a nucleic acid to lactoferrin of 0.10, and a maximum value of the mass ratio of the nucleic acid reagent to the lactoferrin reagent of 6 corresponds to a maximum value of the mass ratio of a nucleic acid to lactoferrin of 6.3. When the purity of the nucleic acid reagent is 90%, a minimum value of the mass ratio of the nucleic acid reagent to the lactoferrin reagent of 0.1 corresponds to a minimum value of the mass ratio of a nucleic acid to lactoferrin of 0.09, and a maximum value of the mass ratio of the nucleic acid reagent to the lactoferrin reagent of 6 corresponds to a maximum value of the mass ratio of a nucleic acid to lactoferrin of 5.7.

Therefore, it has been found that, in the present invention, the effect of a nucleic acid on contributing heat-stability to lactoferrin is appropriately exhibited when the mass ratio of a nucleic acid to lactoferrin is at least in the range of 0.09 to 6.3.

TABLE 3

| pH 6 | Nucleic Acid/Lactoferrin (mass ratio between reagents) | UIBC (%) |
| --- | --- | --- |
| ① | 0 | 55.4 |
| ② | 0.1 | 53.2 |
| ③ | 0.2 | 71.7 |
| ④ | 0.3 | 66.4 |
| ⑤ | 0.4 | 70.8 |
| ⑥ | 0.5 | 86.0 |
| ⑦ | 1 | 96.4 |
| ⑧ | 2 | 80.0 |
| ⑨ | 4 | 78.6 |
| ⑩ | 6 | 69.2 |

TABLE 4

| pH 7 | Nucleic Acid/Lactoferrin (mass ratio between reagents) | UIBC (%) |
| --- | --- | --- |
| ① | 0 | 16.0 |
| ② | 0.1 | 50.4 |
| ③ | 0.2 | 70.9 |
| ④ | 0.3 | 78.3 |
| ⑤ | 0.4 | 74.6 |
| ⑥ | 0.5 | 87.3 |
| ⑦ | 1 | 89.1 |
| ⑧ | 2 | 87.1 |
| ⑨ | 4 | 64.3 |
| ⑩ | 6 | 63.8 |

TABLE 5

| pH 8 | Nucleic Acid/Lactoferrin (mass ratio between reagents) | UIBC (%) |
| --- | --- | --- |
| ① | 0 | 0 |
| ② | 0.1 | 38.8 |
| ③ | 0.2 | 70.0 |
| ④ | 0.3 | 65.4 |
| ⑤ | 0.4 | 73.1 |
| ⑥ | 0.5 | 96.1 |
| ⑦ | 1 | 114.6 |
| ⑧ | 2 | 87.2 |
| ⑨ | 4 | 57.8 |
| ⑩ | 6 | 55.3 |

TABLE 6

| pH 9 | Nucleic Acid/Lactoferrin (mass ratio between reagents) | UIBC (%) |
| --- | --- | --- |
| ① | 0 | 0.0 |
| ② | 0.1 | 12.1 |
| ③ | 0.2 | 70.0 |
| ④ | 0.3 | 74.1 |
| ⑤ | 0.4 | 97.5 |
| ⑥ | 0.5 | 94.1 |
| ⑦ | 1 | 95.1 |
| ⑧ | 2 | 67.9 |
| ⑨ | 4 | 43.9 |
| ⑩ | 6 | 34.7 |

Test Example 3

Test Example 3 was performed to demonstrate that the agent according to the present invention has a greater effect of contributing heat-stability to lactoferrin than conventional art. As a control against the agent according to the present invention, soybean polysaccharide (manufactured by San-Ei Gen F.F.I, Inc. under the trade name of SM-MN-3300) used for stabilizing lactoferrin in the Patent Document 5 (JP-A No. 2004-352669) was used. A nucleic acid reagent and a lactoferrin reagent used in the Test Example 3 were the same as those used in the Test Example 1.

(1) Preparation of Samples

A sample was prepared by adding a nucleic acid reagent and a lactoferrin reagent to purified water so that the mass ratio of the nucleic acid reagent to the lactoferrin reagent was 0.5. On the other hand, another sample was prepared by adding soybean polysaccharide and a lactoferrin reagent to purified water so that the mass ratio of the soybean polysaccharide to the lactoferrin reagent was 0.5.

Each of the samples was adjusted to pH 9 with a 0.1 N sodium hydroxide solution to prepare a test sample.

(2) Test Method

Each of the test samples was subjected to heat treatment by heating at 80° C. for 5 minutes in a water bath (manufactured by HAAKE).

After the completion of the heat treatment, the unsaturated iron binding capacity (UIBC) of lactoferrin contained in each of the test samples was measured by the method described above with reference to the Test Example 2 to determine the heat-stability of the lactoferrin.

(3) Test Results

The results of the Test Example 3 are shown in Table 7. As can be seen from Table 7, the unsaturated iron binding capacity (UIBC) of lactoferrin contained in the heated mixed solution of lactoferrin and a nucleic acid was 82.9%. On the other hand, the unsaturated iron binding capacity (UIBC) of lactoferrin contained in the heated mixed solution of lactoferrin and soybean polysaccharide measured under the same conditions was 12.7%. From the results, it has been confirmed that a nucleic acid used as an active ingredient of the agent for contributing heat-stability to lactoferrin according to the present invention has a greater effect of contributing heat-stability to lactoferrin than soybean polysaccharide.

TABLE 7

| | Agent | Nucleic Acid/ Lactoferrin (mass ratio between reagents) | pH | UIBC (%) |
| --- | --- | --- | --- | --- |
| 1 | Nucleic acid reagent | 0.5 | 9 | 82.9 |
| 2 | Soybean polysaccharide | 0.5 | 9 | 12.7 |

Test Example 4

Test Example 4 was performed to demonstrate that the agent containing a nucleic acid and a metal according to one embodiment of the present invention has a significant effect on contributing heat-stability to lactoferrin.

(1) Preparation of Samples

Ten milligrams of a nucleic acid reagent (manufactured by Nissei Bio Co., Ltd. under the trade name of "DNA-NA SALT", molecular weight: 130 to 150 kpa) and 100 mg of a lactoferrin reagent (manufactured by Milei GmbH under the trade name of "MLF-1") were dissolved in 100 mL of purified water to obtain a solution. Then, the solution was adjusted to pH 7.4 with a 0.1 N sodium hydroxide solution to prepare a test sample. On the other hand, a control sample was prepared by dissolving only a lactoferrin reagent in purified water and adjusting pH to 7.4 with a 0.1 N sodium hydroxide solution.

It is to be noted that the purity of the nucleic acid reagent used was 90 to 100%, and the purity of the lactoferrin reagent was 94.7% (total protein content: 97.5%, ratio of LF to total protein: 97.1%).

(2) Test Method

Test samples were prepared in the same manner as described above, and then copper gluconate (manufactured by Tomita Pharmaceutical Co., Ltd.) was added to the test samples so that the copper concentrations of the test samples were 0, 0.55, and 1.10 µM.

Then, the lactoferrin (LF) content of each of the test samples containing copper gluconate was determined by a latex agglutination test. Then, the test samples and the control sample were subjected to heat treatment by heating at 80° C. for 10 minutes in a water bath (manufactured by TAITEC). After the completion of the heat treatment, these samples were immediately cooled in ice-cold water. Then, the lactoferrin content of each of the cooled samples was measured by a latex agglutination test. The percentage of residual lactoferrin was calculated by the formula:

Percentage of residual lactoferrin=(lactoferrin content after heating/lactoferrin content before heating)× 100%.

It is to be noted that the conditions of the Test Example (e.g., pH and sterilizing temperature) were set to values useful as indicators in actual production of foods and beverages.

(3) Test Results

The results of the Test Example 4 are shown in Table 8. In Table 8, lactoferrin is abbreviated as "LF".

As can be seen from Table 8, the percentage of residual lactoferrin of the test sample to which neither nucleic acid nor copper was added was as low as 4.5%. On the other hand, the percentage of residual lactoferrin of the test sample to which a nucleic acid was added so that a weight ratio of nucleic acid to lactoferrin was 0.1 was 21.6%.

The percentage of residual lactoferrin of the test sample to which copper was added in addition to a nucleic acid so that the molar ratio of copper to lactoferrin was 0.04 was 26.5%, which was 123% as compared to the percentage of residual lactoferrin of the test sample to which only a nucleic acid was added. The percentage of residual lactoferrin of the test sample to which copper was also added so that the molar ratio of copper to lactoferrin was 0.09 was 35.7%, which was 165% as compared to the percentage of residual lactoferrin of the test sample to which only a nucleic acid was added.

From the results, it has been found that addition of copper to lactoferrin in the presence of a small amount of nucleic acid significantly improves the percentage of residual lactoferrin.

It is to be noted that the same test was performed using ferrous sulfate (as iron) and zinc gluconate (as zinc) instead of copper gluconate (as copper). As a result, in either case, the percentage of residual lactoferrin was increased as in the case of adding copper.

TABLE 8

Relationship between addition of nucleic acid and copper and percentage of residual lactoferrin (%)

| Copper/LF (molar ratio) | Nucleic acid/LF (weight ratio) | |
|---|---|---|
| | 0 | 0.1 |
| 0 | 4.5% | 21.6% |
| 0.04 | — | 26.5% |
| 0.09 | — | 35.7% |

INDUSTRIAL APPLICABILITY

The agent for contributing the heat-stability of lactoferrin (agent for stabilizing lactoferrin against heat treatment) according to the present invention improves the heat-stability of lactoferrin in a pH range from slightly acidic to alkaline, thereby making it possible to heat-sterilize lactoferrin without thermally-denaturing or deactivating it. Further, addition of lactoferrin together with the agent for stabilizing lactoferrin against heat treatment to products, such as foods, beverages, feeds, and pharmaceutical products, requiring sterilization makes it possible to directly sterilize these products by heating in the last stage of their production processes. This makes it possible to provide a method for easily producing a product containing lactoferrin.

The invention claimed is:

1. A method for stabilizing lactoferrin against heat treatment comprising:
    adding a nucleic acid composition to lactoferrin,
    wherein the nucleic acid composition comprises DNA having a molecular weight of 5 kDa to 12,000 kDa, and
    wherein a mass ratio of the nucleic acid mass to the lactoferrin mass is in a range of 0.09 to 6.3.

2. A method for heat-sterilizing lactoferrin, comprising:
    stabilizing lactoferrin against heat treatment by
    adding a nucleic acid composition to lactoferrin; and
    heat-sterilizing the thermally-stabilized lactoferrin,
    wherein the nucleic acid composition comprises DNA having a molecular weight of 5 kDa to 12,000 kDa, and
    wherein a mass ratio of the nucleic acid mass to the lactoferrin mass is in a range of 0.09 to 6.3.

3. The method according to claim 1 or 2, wherein the nucleic acid composition further comprises a metal.

4. The method according to claim 3, wherein the metal is at least one selected from the group consisting of iron, zinc, and copper.

5. The method according to claim 1 or claim 2, wherein the nucleic acid composition further comprises a pH adjusting component.

6. The method according to claim 1 or claim 2, wherein the DNA of said nucleic acid composition has a molecular weight of 60 kDa to 12,000 kDa.

7. The method according to claim 1 or claim 2, wherein the DNA of said nucleic acid composition is derived from a natural source.

8. The method according to claim 1 or claim 2, wherein the DNA of said nucleic acid composition is derived from milt.

9. The method according to claim 1 or claim 2, wherein a nucleic acid content of the nucleic acid composition is in the range of 60% to 100%.

10. The method according to claim 1, further comprising:
adjusting a pH of lactoferrin into a pH range of 6 to 10.

11. The method according to claim 2, wherein the step of stabilizing lactoferrin further comprises:
adjusting a pH of lactoferrin into a pH range of 6 to 10.

* * * * *